US006907351B2

(12) United States Patent
Julia et al.

(10) Patent No.: US 6,907,351 B2
(45) Date of Patent: Jun. 14, 2005

(54) CUSTOMER-BASED PREDICTION METHOD AND SYSTEM USING NEAR INFRARED REFLECTANCE SPECTRA OF MATERIALS

(75) Inventors: Thierry Julia, La Garenne Colombes (FR); Jean-Christophe Bodin, Monlucon (FR)

(73) Assignee: Aventis Animal Nutrition S.A., Antony (FR)

( * ) Notice: Subject to any disclaimer, the term of this patent is extended or adjusted under 35 U.S.C. 154(b) by 153 days.

(21) Appl. No.: 09/918,512

(22) Filed: Aug. 1, 2001

(65) Prior Publication Data

US 2003/0028328 A1 Feb. 6, 2003

(51) Int. Cl.[7] .......................... G01N 31/00; G06F 19/00

(52) U.S. Cl. ............................ 702/23; 702/28; 702/30; 436/8; 436/86

(58) Field of Search .............................. 702/22–25, 28, 702/30–32, 108, 121–123, 127; 250/339.09, 339.12; 436/8, 86, 164, 171; 705/1, 10, 16, 20

(56) References Cited

U.S. PATENT DOCUMENTS

| | | | | |
|---|---|---|---|---|
| 3,776,642 A | * | 12/1973 | Anson et al. | 356/418 |
| 4,893,253 A | * | 1/1990 | Lodder | 702/28 |
| 5,219,400 A | * | 6/1993 | Jacot et al. | 600/320 |
| 5,223,714 A | | 6/1993 | Maggard | 250/343 |
| 5,362,965 A | | 11/1994 | Maggard | 250/339.12 |
| 5,452,232 A | | 9/1995 | Espinosa et al. | 702/30 |
| 5,475,612 A | | 12/1995 | Espinosa et al. | 700/268 |
| 5,490,085 A | | 2/1996 | Lambert et al. | 700/266 |
| 5,506,117 A | | 4/1996 | Andrews et al. | 435/29 |
| 5,712,797 A | | 1/1998 | Descales et al. | 702/30 |
| 5,717,209 A | | 2/1998 | Bigman et al. | 250/339.1 |
| 5,723,338 A | | 3/1998 | Rutledge et al. | 436/56 |
| 5,729,740 A | * | 3/1998 | Tsumura | 707/104.1 |
| 5,740,073 A | | 4/1998 | Bages et al. | 702/30 |
| 5,763,883 A | | 6/1998 | Descales et al. | 250/339.09 |
| 5,832,182 A | * | 11/1998 | Zhang et al. | 706/50 |
| 5,843,783 A | | 12/1998 | Rutledge et al. | 436/56 |
| 5,861,228 A | | 1/1999 | Descales et al. | 436/171 |
| 5,928,954 A | | 7/1999 | Rutledge et al. | 436/56 |
| 5,935,863 A | | 8/1999 | Descales et al. | 436/171 |
| 5,991,739 A | * | 11/1999 | Cupps et al. | 705/26 |
| 6,070,128 A | | 5/2000 | Descales et al. | 702/30 |
| 6,496,309 B1 | * | 12/2002 | Bliton et al. | 359/618 |
| 6,512,577 B1 | * | 1/2003 | Ozanich | 356/73 |
| 2001/0032185 A1 | * | 10/2001 | Masaki | 705/52 |
| 2002/0138546 A1 | * | 9/2002 | Parsonnet et al. | 709/200 |

FOREIGN PATENT DOCUMENTS

| | | |
|---|---|---|
| DE | 298 09 591 | 11/1998 |
| WO | WO 97 21091 | 6/1997 |
| WO | WO 01/15548 | 3/2001 |
| WO | WO01/15548 A1 * | 3/2001 |

OTHER PUBLICATIONS

Copy of co–pending U.S. Appl. No. 09/653,549, filed on Aug. 31, 2000.

(Continued)

*Primary Examiner*—Marc S. Hoff
*Assistant Examiner*—Manuel L. Barbee
(74) *Attorney, Agent, or Firm*—Finnegan, Henderson, Farabow, Garrett & Dunner, L.L.P.

(57) ABSTRACT

A method and system for predicting the content level of components in materials based on the response of the materials to near infrared radiation. One embodiment comprises electronically receiving a near infrared reflectance spectrum of a material from a customer, predicting the content level of a component in the material based on the spectrum, and electronically reporting the prediction to the customer. Another embodiment includes the exchange of the customer request and prediction report on a Web site or by electronic mail. Other embodiments include the prediction reports, and uses of the predictions, for example in quality control and toxicity evaluation.

20 Claims, 8 Drawing Sheets

OTHER PUBLICATIONS

Copy of co–pending U.S. Appl. No. 09/918,483, filed on Aug. 1, 2001.

Van Kempen et al., "Near–Infrared Reflectance Spectroscopy in Precision Feed Formulation", J. Appl. Poultry Res. 6: 471–477 (1997).

Van Kempen et al., "NIRS May Provide Rapid Evaluation of Amino Acids", Feedstuffs, Dec. 2, 1996.

Amino News, vol. 1, No. 3, Dec. 2000.

T. Hancewicz et al., "Quantitative Analysis of Vitamin A Using Fourier Transform Raman Spectroscopy", May 4, 1995, Spectrochimica Acta, vol. 51, pp. 2193–2198.

Derwent Abstract of DE 298 09 591.

R. J. van Barneveld, "Characteristics of feed grains that influence their nutritive value and subsequent utilisation by pigs", Proceeding of the Sixth Biennial Conference of the Australasian Pig Science Association APSA held in Canberra, ACT on Dec. 7 to 10, 1997, pp. 193–207.

* cited by examiner

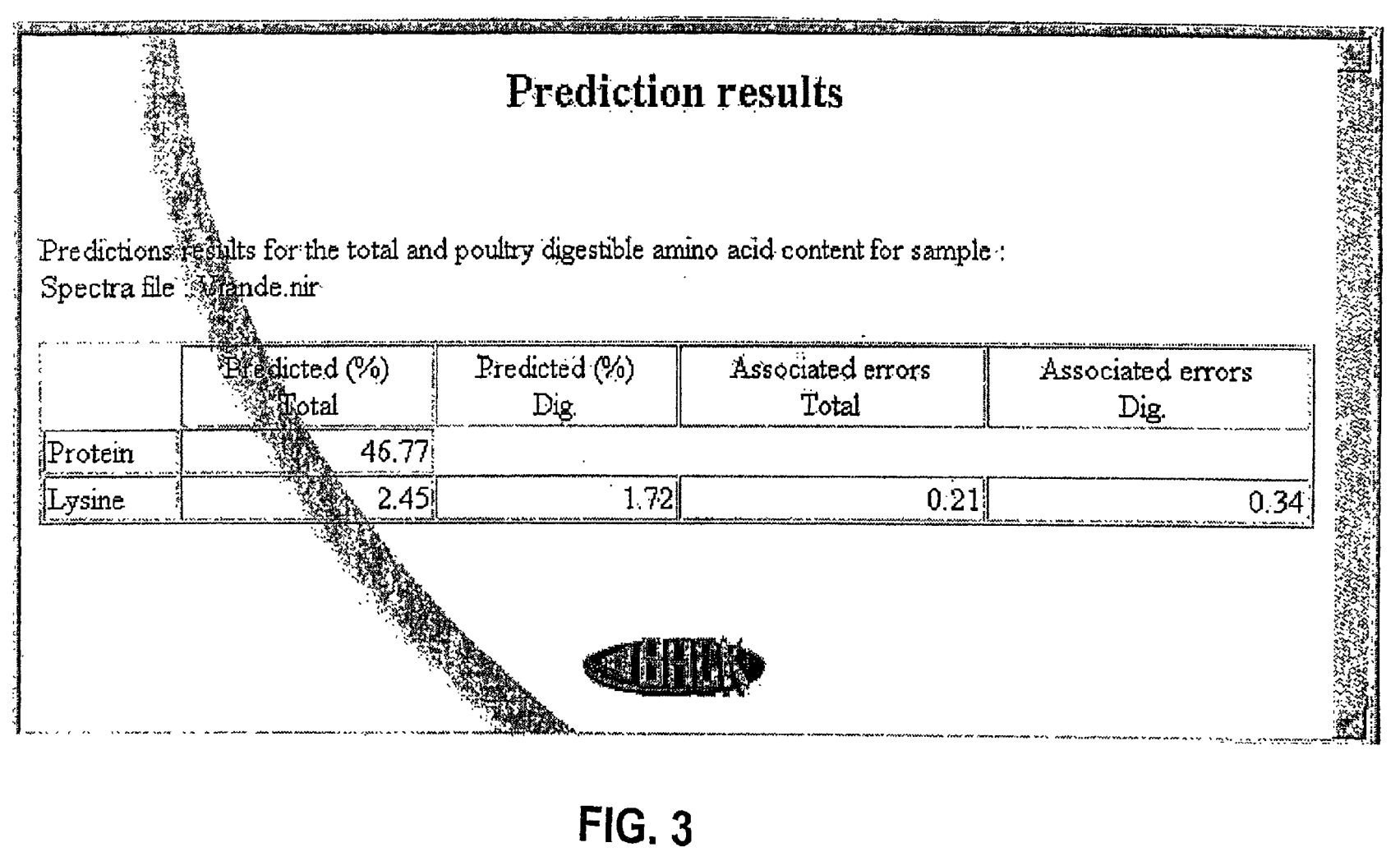

Prediction results

Predictions results for the total and poultry digestible amino acid content for sample :
Spectra file : Viande.nir

| | Predicted (%) Total | Predicted (%) Dig. | Associated errors Total | Associated errors Dig. |
|---|---|---|---|---|
| Protein | 46.77 | | | |
| Lysine | 2.45 | 1.72 | 0.21 | 0.34 |

FIG. 3

Prediction results for the total and digestible amino acid content for sample:

RPAN ID code.
Customer ID code:

| | Predicted (%) | | RMSEP | |
|---|---|---|---|---|
| | Total | Dig. | Total | Dig. |
| Protein | 62.7 | | 2.7 | |
| Lysine | 2.79 | 1.79 | 0.25 | 0.29 |
| Methionine | 0.87 | 0.64 | 0.11 | 0.11 |
| Cysteine | 2.00 | 1.26 | 0.20 | 0.16 |
| Sulfur AA | 2.83 | 1.82 | 0.15 | 0.17 |
| Threonine | 2.96 | 2.06 | 0.13 | 0.15 |
| Tryptophan | 0.69 | 0.49 | 0.08 | 0.08 |
| Valine | 4.31 | 3.08 | 0.20 | 0.22 |
| Isoleucine | 2.83 | 2.13 | 0.21 | 0.22 |
| Leucine | 4.87 | 3.67 | 0.28 | 0.31 |
| Phenylalanine | 2.81 | 2.06 | 0.16 | 0.23 |
| Histidine | 1.63 | 1.29 | 0.23 | 0.24 |
| Arginine | 3.93 | 3.21 | 0.46 | 0.48 |

AAdigestimator 73

Spectral Prox. 1.5

NOTES
- Results provided are predictions and not actual analytical values.
- RMSEP= measure of expected variation of prediction
- Predictions are prepared using Calibration version No. 1.01
- AAdigestimator is an index for the digestibility of the average essential amino acid and may be used to compare digestibility of similar samples. Digestibility coefficients calculated for individual amino acids are not meaningful since predictions for total and digestible amino acids are independent.
- Sulfur AA is predicted independent of methionine and cysteine.

FIG. 4

Prediction results history

| Date | File | Results |
|---|---|---|
| Tue, March 5th, 2001 | Cereal.nir | Ground hay |
| Fri, March 9th, 2001 | Corn.nir | Silage corn |

Click on the file name to see the prediction results.

FIG. 5

CUSTOMER-BASED PREDICTION METHOD AND SYSTEM USING NEAR INFRARED REFLECTANCE SPECTRA OF MATERIALS

FIELD OF THE INVENTION

This invention relates to methods and systems for predicting the content level of components in materials, using the response spectra of the materials to near infrared radiation. The invention also relates to customer-based prediction methods and systems, including methods and systems that are adapted to provide prediction reports for selected materials.

BACKGROUND

Materials such as animal feeds, feedstuffs, and pharmaceutical and cosmetic compositions contain a variety of components. In the animal feed industry, for example, an animal feed may contain protein, amino acids, vitamins and minerals, among other things. In the pharmaceutical and cosmetic industries, compositions can contain one or more active ingredients together with various excipients and additives. Control and monitoring of the composition of such materials has a number of advantages. For example, proper control over the nutrient composition of animal feeds assists in the healthy and efficient growth of the animals. Likewise, monitoring the composition of pharmaceutical or cosmetic compositions over time, for instance during storage, assists in evaluating the stability of the materials.

At least in the animal feed industry, raw materials for use in feeds can vary significantly in composition. In fact, the content level of any given component in a material typically varies within certain tolerance limits about an average value among different samples of the material. Those variations render it difficult to include all desired levels of components in an animal's diet. One attempt at ensuring those desired levels includes assessing the natural variation of component levels in a material, and adding supplemental components to all batches of the material to achieve a guaranteed high level of the component. This technique does not reduce the natural variation in the component levels. Instead, it simply raises the average level of the component to a higher average level. Thus, some batches of the raw material will still contain less than needed levels of components. Other batches, on the other hand, will contain excess levels of component. In the case of excess nutrient in an animal feed, for example, that can lead to extra cost and higher levels of pollution in the form of nitrogen and phosphorus in the manure of animals fed those diets.

Another attempt at ensuring desired levels of components in animal feed involves measuring the levels of the component in batches of material, and either supplementing that level where necessary with additional components or directing the material into an application that can favorably use the material as it is. Success in such a process depends in large part on the accuracy and ease of the measurement of the component levels. The most favorable measurement is both accurate and fast. That applies as well to measurements in other industries, for example the pharmaceutical and cosmetic industries.

One method of determining the content levels of components in materials is by physical examination or testing and quantification of the components of interest. In the field of feedstuffs, those techniques are referred to as "wet chemistry" or in vitro determinations. In vitro techniques may also determine compositions of pharmaceutical or cosmetic materials. Although accurate in determining certain component levels in materials, these techniques are time consuming.

Another method for measuring the content levels of components in materials involves predicting those levels based on the near infrared reflectance spectrum ("NIRS") of the materials. A material subjected to near infrared radiation will emit a response to the radiation, which may be plotted in the form of a spectrum. A regression technique may correlate a given response spectrum of a material to reference data such as a known content levels of a component in the material. The content level of the component in a new sample of material may then be predicted by obtaining the near infrared spectrum of the material and applying the relevant correlation.

Regression techniques like that described above can be used, for example, by a feed mill, to predict the protein, amino acid, moisture, fat, and ash contents of feedstuffs, as discussed in Van Kempen and Simmins, "Near-infrared Reflectance Spectroscopy in Precision Feed Formulation," J. Appl. Poultry Res., vol. 6, pp 471–475 (1997) and Van Kempen and Jackson, "NIRS May Provide Rapid Evaluation of Amino Acids," Feedstuffs (Dec. 2, 1996). Co-pending U.S. patent application Ser. No. 09/471,420, filed on Dec. 23, 1999, also discusses a method of predicting the content level of vitamins in materials using a regression technique. The contents of the three above-cited documents are expressly incorporated herein by reference in their entireties. These techniques require an initial investment by the user to establish the appropriate database calibration between near infrared spectra of the materials and the content levels of components in the materials.

A service for amino acid predictions in raw materials using NIRS is discussed in AminoNews, vol. 1, no. 3, pp. 11–14 (December 2000), the contents of which are expressly incorporated herein by reference in its entirety. This service is described as requiring a period of a few days for analysis of the material of interest. That delay can include time for shipping samples of material to the service provider for analysis. Use of this service also involves an economic cost for shipping the materials, as well as possible delay and extra documentation for shipping materials through customs when mailing internationally. The calibration sets for this service are disclosed as generated using wet chemistry analysis correlated with near infrared spectra of the materials.

SUMMARY OF THE INVENTION

Methods and systems consistent with the principles of the invention predict the content level of components in materials. Such methods and systems can provide customers with information regarding the content level of components in the materials through electronic communication. For example, in accordance with the principles of the present invention, one embodiment of a method comprises:

- electronically receiving a request from a customer to predict the content level of at least one component in a material, wherein the request includes a near infrared reflectance spectrum of the material;
- comparing the spectrum to a database calibration that correlates known content levels of the component in other material to known near infrared reflectance spectra of the other material;
- predicting the content level of the component; and
- electronically reporting the prediction to the customer.

Other embodiments of the invention include the exchange of the customer request and prediction report on a Web site or by electronic mail. Another embodiment of the invention includes a method and system for predicting the content levels of components in a feedstuff or animal feed. Other embodiments include a menu structure for selection of items by the customer in making a request, and a fee structure for payment by the customer for the predictions. Still other embodiments include uses of the predictions, such as in quality control and toxicity evaluation.

BRIEF DESCRIPTION OF THE DRAWINGS

The accompanying drawings, which are incorporated in and constitute part of this specification, illustrate various features and aspects of the invention and, together with the text of the specification, serve to explain various principles of the invention. The invention as claimed is not limited to embodiments illustrated in the drawings.

FIG. 3 illustrates an exemplary Web-based prediction report, according to the principles of the invention.

FIG. 4 illustrates an exemplary prediction report, according to the principles of the invention, which can be sent to a customer as an attachment by electronic mail.

FIG. 5 illustrates an exemplary Web-based screen offering a history of customer requests and prediction reports, stored according to the principles of the invention.

DETAILED DESCRIPTION OF THE INVENTION

This invention relates to methods and systems for predicting the content levels of components in materials. The methods and systems allow for accurate and fast predictions based on analysis of the near infrared reflectance spectrum of the materials. Customers using the methods and systems receive predictions made with the benefit of a central database and, therefore, need not invest for themselves in creating their own individual spectra calibrations. Customers may also send their requests and receive prediction reports electronically, providing for fast and convenient analysis of the materials.

In accordance with the principles of the invention, one embodiment is a method that comprises:

- electronically receiving a request from a customer to predict the content level of at least one component in a material, wherein the request includes a near infrared reflectance spectrum of the material;
- comparing the spectrum to a database calibration that correlates known content levels of the component in other material to known near infrared reflectance spectra of the other material;
- predicting the content level of the component; and
- electronically reporting the prediction to the customer.

Figure 1:
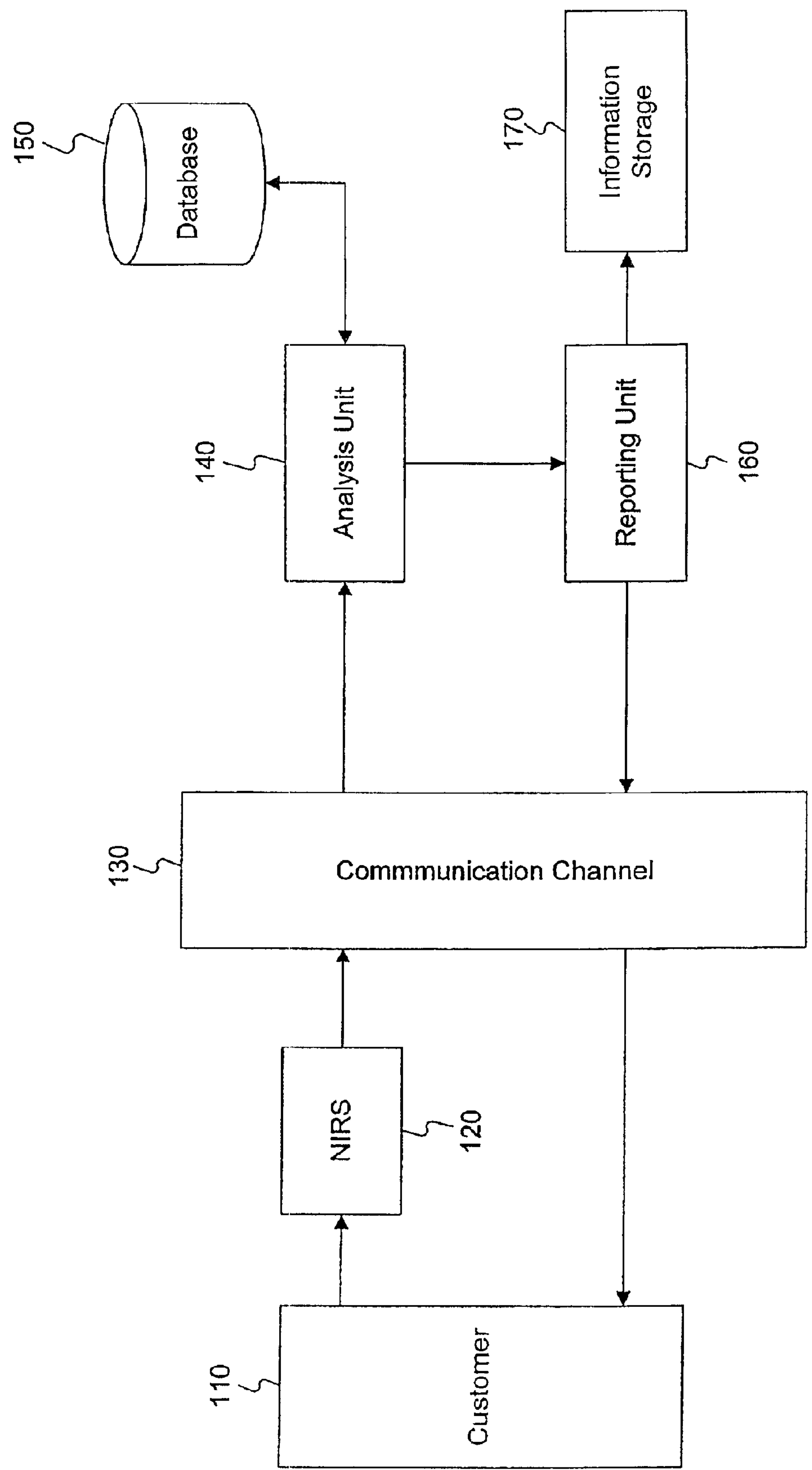
FIG. 1 illustrates a block diagram of an exemplary system environment for implementing various features and aspects of the invention.

FIG. 1 illustrates a block diagram of an exemplary system environment that can be used in this method, as well as other aspects and features of the invention. The various components illustrated in FIG. 1 may be implemented through any suitable combination of hardware, firmware and/or software in accordance with the features and functionality described below.

The principles of the invention, including the noted method, may be applied to a wide array of materials. The "material" may be any substance that responds to near infrared radiation. For example, the material may be a feedstuff or an animal feed. Further example materials include cereal, corn, soybean cake, oleoproteinaceous flour, animal meal, animal byproduct, fish meal, cereal byproduct and silage corn. Other materials include pharmaceutical compositions, cosmetic compositions, and food articles for human consumption.

The "component" studied in the material includes any component whose content level can correlate with near infrared spectra of materials containing the component. For example, the component may be a nutrient. Further example components include protein, total or digestible amino acids, gross or metabolizable energy, total or retained phosphorous and silage corn. Further components include methionine, lysine, cystine, threonine, tryptophane, valine, isoleucine, phenylalanine, histidine and arginine. Other components include toxins, such as mycotoxins, and impurities. Still other components include active or inactive ingredients in pharmaceutical or cosmetic compositions. The determination of "content level" of the component may be expressed, for example, as a weight percent or in a number of parts such as parts per hundred, parts per thousand, or parts per million. The content level may also be zero, meaning that the material does not contain the component.

Referring to FIG. 1, a "customer" 110 is illustrated. Although only one customer is shown in FIG. 1, it will be appreciated that multiple customers may be supported and provided in the system environment. The customer includes any person, company, or other entity capable of submitting the request. Customers include, for example, manufacturers of animal feeds or feedstuff for animals, cattle, pets, or fish. A customer may also be a producer or storage company for agricultural raw materials, or a retailer, importer or exporter of raw materials. Customers also include processors of raw materials or meat products.

Customer 110 may create the near infrared spectra using any appropriate NIRS equipment 120 for generating near infrared spectra of materials. Exemplary equipment includes scanning models marketed by Foss, Bran & Luebbe, Hewlett Packard, Hitachi, Perten, Bömen and Zeiss. The customer itself may generate the spectrum from the material using NIRS equipment 120, or may instead send the material to a third party to scan the sample to a near infrared spectrum using NIRS. The third party may submit the spectrum and request on behalf of the customer, or may return the spectra to the customer for the customer to submit. The third party may also be the recipient of the prediction results, then forwarding the results to the customer.

In FIG. 1, customer 110 may submit one spectrum and request at a time, or may submit multiple spectra and requests at a time. The customer may also request analysis of the content levels of multiple components in any given material. The customer may also submit multiple requests, with the requests varying in terms of the predictions desired. The customer request may be sent and received electronically in analysis unit 140 through a communication channel 130. Communication channel 130 may include wired or wireless technologies and/or public communication networks, such as the Internet or a public switched telephone network. For example, the spectrum and request may be received from the customer on a Web site or by electronic mail. Such a Web site may be hosted by a Web server that is provided as part of analysis unit 140 or separately connected to communication channel 130.

Each of the components directly or indirectly connected to communication channel 130 may include appropriate hardware and/or devices for receiving and transmitting information or files through communication channel 130. For example, customer 110 may include a personal computer, a workstation or other devices capable of communicating via communication channel 130. The same is also true for analysis unit 140 and reporting unit 160. Communication software (such as a Web browser or an electronic mail application software) may also be provided in each of the components connected to communication channel 130.

Figure 2:
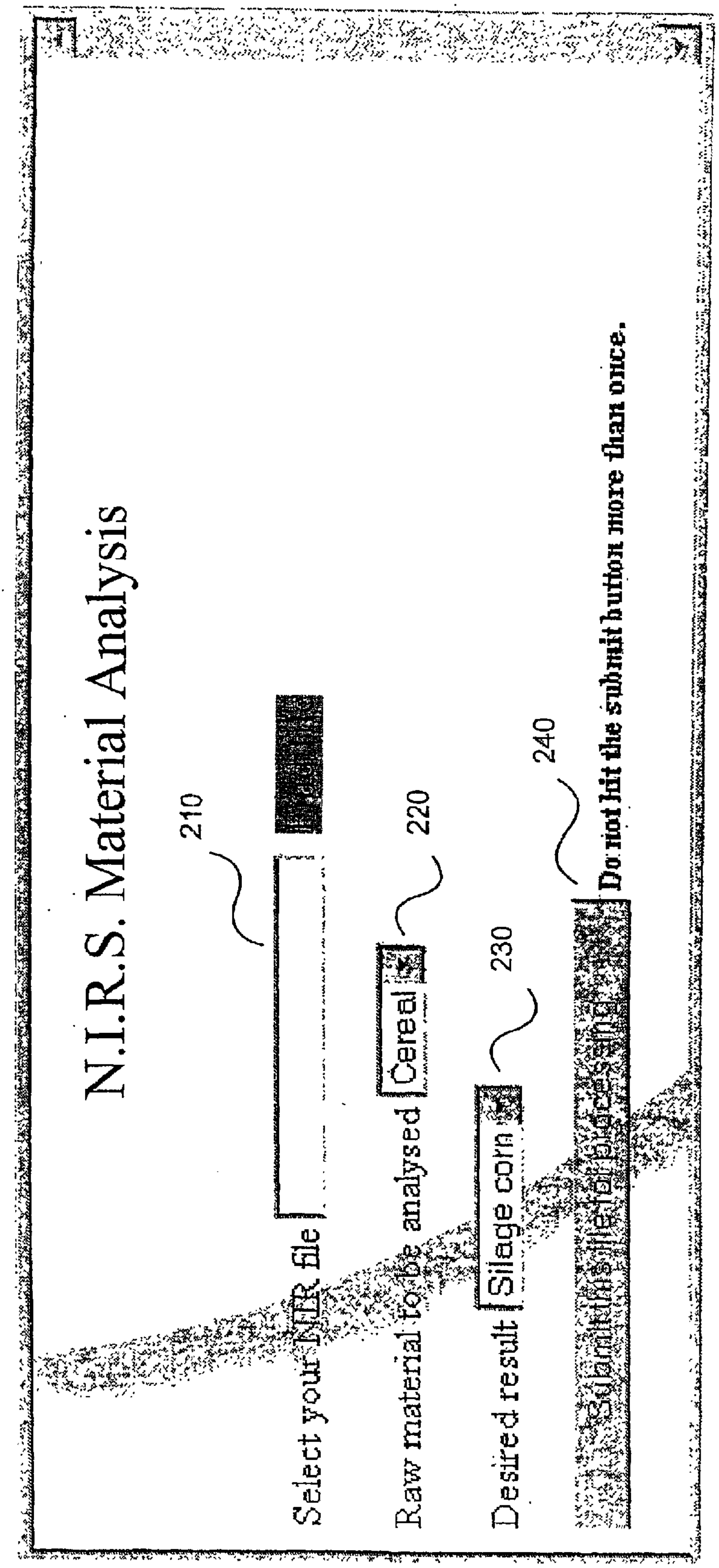
FIG. 2 illustrates an exemplary Web-based and menu-driven screen for a customer making a request, according to the principles of the invention.

The request from each customer 110 may include information relating to, for example, the spectrum, the file type of the spectrum, the material represented by the spectrum, the component to be analyzed, and the format of the prediction report desired. That information may be provided, for example, by customer selection of relevant items from one or more menu options provided to the customer. FIG. 2 illustrates an exemplary Web-based and menu-driven screen for a customer making a request. Possible menu options illustrated in FIG. 2 include, for example, the file type of the spectra 210, the category of material represented by the spectrum 220, and the one or more components whose content level is to be predicted 230. The screen may also require the customer to affirmatively select a command 240 to finalize the request.

The file type of the spectra from the customer may differ depending on the model of equipment used to produce the spectra. For example, files created by Foss equipment carry the designation ".nir," and files created by Bran & Luebbe equipment carry the designation ".spf." The calibrations present in the database may be based on, for example, a single file type, such as JCAMP, .nir or .spf. In order to perform the appropriate comparison of the spectra to the database, a customer spectra may be converted to the file type used in the calibrations. An .nir file may be converted to, for example, an international format such as JCAMP, which may then be converted, if desired, to an .spf file. Such file conversion may be performed, for example, by analysis unit 140.

The spectra received from customer 110 may also require a mathematical correction to standardize the NIRS equipment 120 used in generating the spectra with the spectra in database 150. Such a standardization can be performed, for example, upon first receipt of a spectra from a particular piece of equipment and periodically, for example every 12 to 18 months, in the future. The standardization may be executed, for example, by recording thirty-five reference spectra on the customer apparatus and on the "master" apparatus of database 150, and creating a standardization file which, when applied to the files of spectra coming from the customer, will convert the files to render them compatible with the database calibrations.

Figure 8:
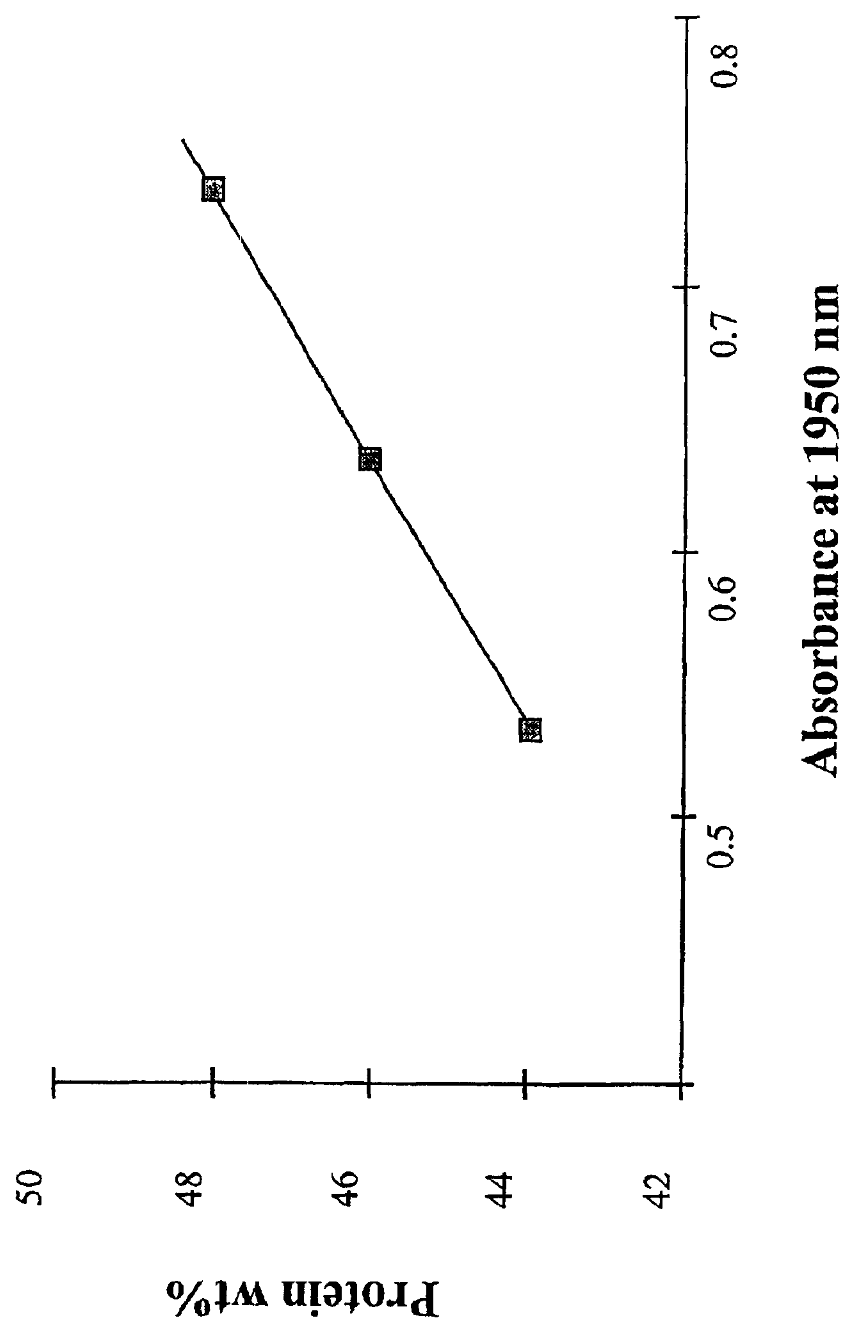
FIG. 8 illustrates an exemplary calibration for prediction of protein content in samples of soyabean meal using NIRS.

The spectrum received from the customer is then compared in analysis unit 140 to a calibration in database 150 that correlates known content levels of the component in other material to known near infrared reflectance spectra of the other material. The underlying calibrations in the database may be established in a number of ways, including the techniques discussed in Van Kempen and Simmins, "Near-Infrared Reflectance Spectroscopy in Precision Feed Formulation," J. Appl. Poultry Res., vol. 6, pp 471–475 (1997) and Van Kempen and Jackson, "NIRS May Provide Rapid Evaluation of Amino Acids," Feedstuffs (Dec. 2, 1996), and co-pending U.S. patent application Ser. No. 09/471,420 discussed above. In accordance with the principles of the invention, the calibrations can be made by determining the relevant component levels in various different samples of a material, and correlating those known levels with the near infrared spectra of the materials. For example, FIG. 8 illustrates an exemplary calibration for prediction of protein content in samples of soyabean meal using NIRS.

Database 150 may contain one or more different calibrations. The appropriate calibration may be selected based on the substance of the customer request. Database 150 may contain calibrations for any number of materials and any number of components whose content level is to be predicted. The database may contain calibrations based on prior in vitro measurements (such as measurements by wet chemistry) or in vivo measurements correlated with near infrared reflectance spectra of the relevant materials. The database may contain, for example, calibrations based on prior in vivo measurement for calibrations to predict, for example, content levels of digestible nutrients and metabolizable energy. The database calibrations may also be based on a wide variety of samples taken from geographically diverse regions, even of world-wide origin, and may contain calibrations of materials grown and produced in different seasons of the year.

Calibrations in database 150 may be specific to the category of material to be analyzed. For example, a database calibration of methionine content in soyabean meal to spectra of the material may be used in a prediction of methionine content in a sample of soyabean meal. A different calibration may likewise be used for predicting lysine content in the soyabean meal, or for predicting methionine content in corn. Alternatively, the database calibration may not be specific to the category of material to be analyzed, but still may nonetheless be useful for the prediction. For example, a general database calibration for methionine content may be used in a prediction of methionine content in a sample of any material.

Analysis unit 140 determines, in light of the customer request, the appropriate calibration to apply to the particular material and component to be analyzed. If more than one component content level is to be predicted, the analysis unit may select different calibrations for each determination and thus may perform multiple analyses using multiple calibrations. Upon selection of the appropriate calibrations, the comparison in analysis unit 140 of a given spectrum to the calibration may be performed, for example, by a computer-based platform, leading to a prediction of the content level of the component studied. Appropriate software for comparing a given spectra to a calibration and reaching the prediction is commercially available, such as from Bran & Luebbe and Foss.

The comparison of the spectra to the relevant calibration produces a prediction of the component level in the material. The prediction may also include an associated degree error in the prediction. That error may take into account, for example, error in the underlying data used to build the relevant calibration, and error associated with applying NIRS as a predictor of the composition of the material. The prediction may be expressed, for example, together with a particular confidence interval.

Once analysis unit 140 obtains the relevant prediction, a reporting unit 160 then reports the prediction results to customer 110 through communication channel 130. The communication to customer 110 may include wired or wireless technologies and/or public communication networks, such as the Internet or a public switched telephone network. For example, the report may be provided via a Web site or electronic mail. FIG. 3 illustrates an exemplary Web-based prediction report. In FIG. 3, an exemplary report is illustrated of the prediction of total protein, total lysine, and digestible lysine for a material, together with the associated errors for each prediction. Using electronic mail, the report may also be sent to customer 110, for example, as a reference to an HTML page, in text format, or as an attachment such as a Microsoft Excel document or word processing document. For instance, FIG. 4 illustrates an exemplary prediction report, according to the principles of the invention, as an attachment by electronic mail. In FIG. 4, an exemplary report is illustrated that can be sent to a customer of the prediction of multiple component content levels in a material, together with the appropriate degree of error for each measurement.

Methods and systems of the invention consistent with the principles of the invention include, but are not limited to, fully automated methods and systems for providing service to a customer, wherein the receipt and processing of the customer request, and the analysis and reporting of results to the customer are performed without human involvement. The electronic exchange of information with the customer, together with an automated computer analysis of the spectrum and reporting of results, allows for fast determination and reporting of the prediction. Consistent with the principles of the invention, the report may be sent to the customer within, for example, 24 hours, or within 10 minutes of the customer request. An automated application of the appropriate calibration to the customer spectrum also allows for 24 hours access of the automated service to the customer.

Any information received or sent to the customer, or generated in the processing of the spectra, may be stored or later destroyed. For example, any such information may be stored in an information storage 170, for example by reporting unit 160. That information can be organized in any fashion, for example organized into sub-storage units specific to each customer. Such information may be made retrievable to the customer. Stored information may be retrievable by the customer on a Web site or otherwise upon request. Information that may be stored includes any customer requests, including spectra, and prediction reports. Other information that may be stored include the dates of particular requests, the status of any particular requests (in progress, complete, etc.) and the number of requests submitted within a certain period of time. FIG. 5 illustrates an exemplary Web-based screen offering a history of customer requests and prediction reports stored according to the principles of the invention. In FIG. 5, an illustration is provided of two particular past requests of a customer, and details of the requests. Such a prediction history screen allows the customer to view the prediction results via a Web site or through a document sent by electronic mail.

Stored information need not be available for retrieval by the customer. For example, information relating to the calibration set chosen for the prediction, or any record of mathematical corrections made to customer spectra, or details of file conversion of a customer's spectra, or other such technical information may be useful for storage and for retrieval but may not necessarily be of importance to the customer. Information concerning any fees charged to the customer for predictions may also be stored. As with all other information, any fee information may be accessible to the customer or may not be made accessible to the customer.

Figure 6:
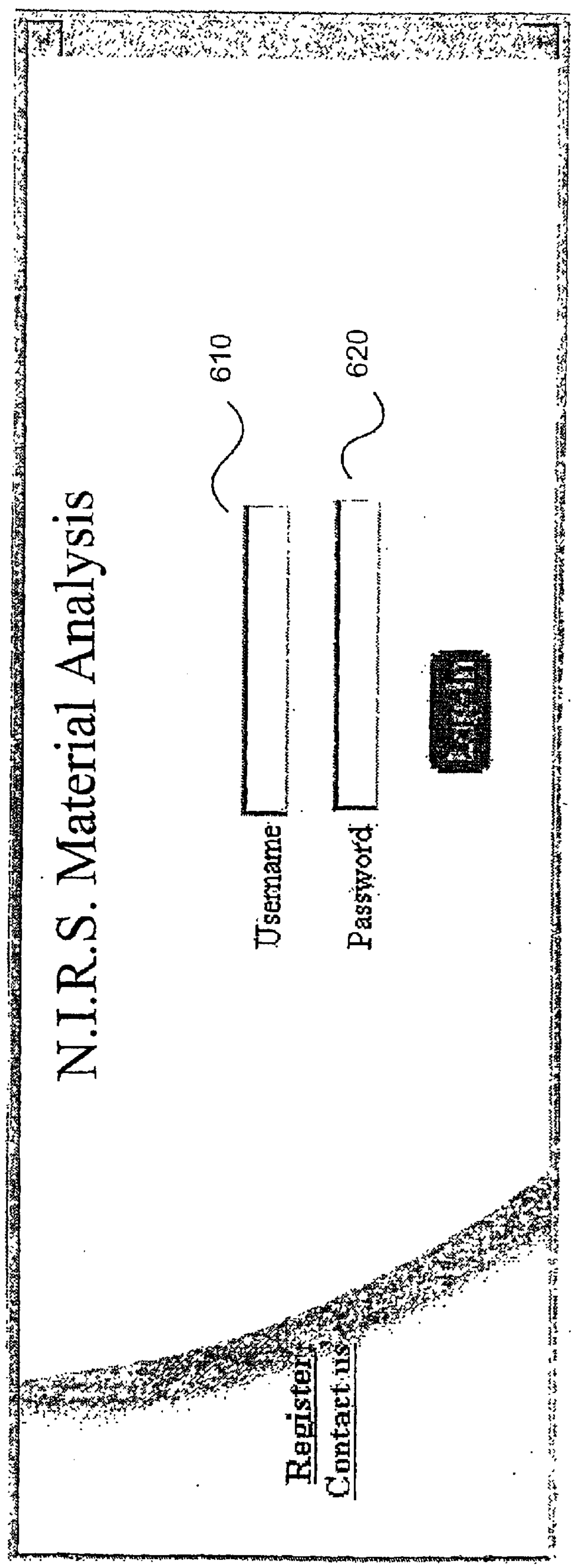
FIG. 6 illustrates an exemplary Web-based login screen for a customer making a request, according to the principles of the invention.

Other embodiments of the invention include opening a customer account for the customer who wishes to obtain NIRS predictions. Such a task could be performed, for example, by analysis unit 140 upon first receipt of a request from a given customer. The opening of the customer account may include, for example, providing the customer with identity and/or security passwords. The customer could use such passwords, for example, when making requests for predictions or accessing stored information relating to past requests. FIG. 6 illustrates an exemplary Web-based login screen for a customer making a request or requesting access to stored information relating to past requests. FIG. 6 illustrates a login screen requiring entry of a username 610 and password 620. The identity and security passwords may be verified, for example, before processing a request or allowing access to stored information. In the event that the requester does not have the appropriate credentials, the requester can be notified, for example by an error message. Such an error message may also include information on how to establish a customer account.

Figure 7:
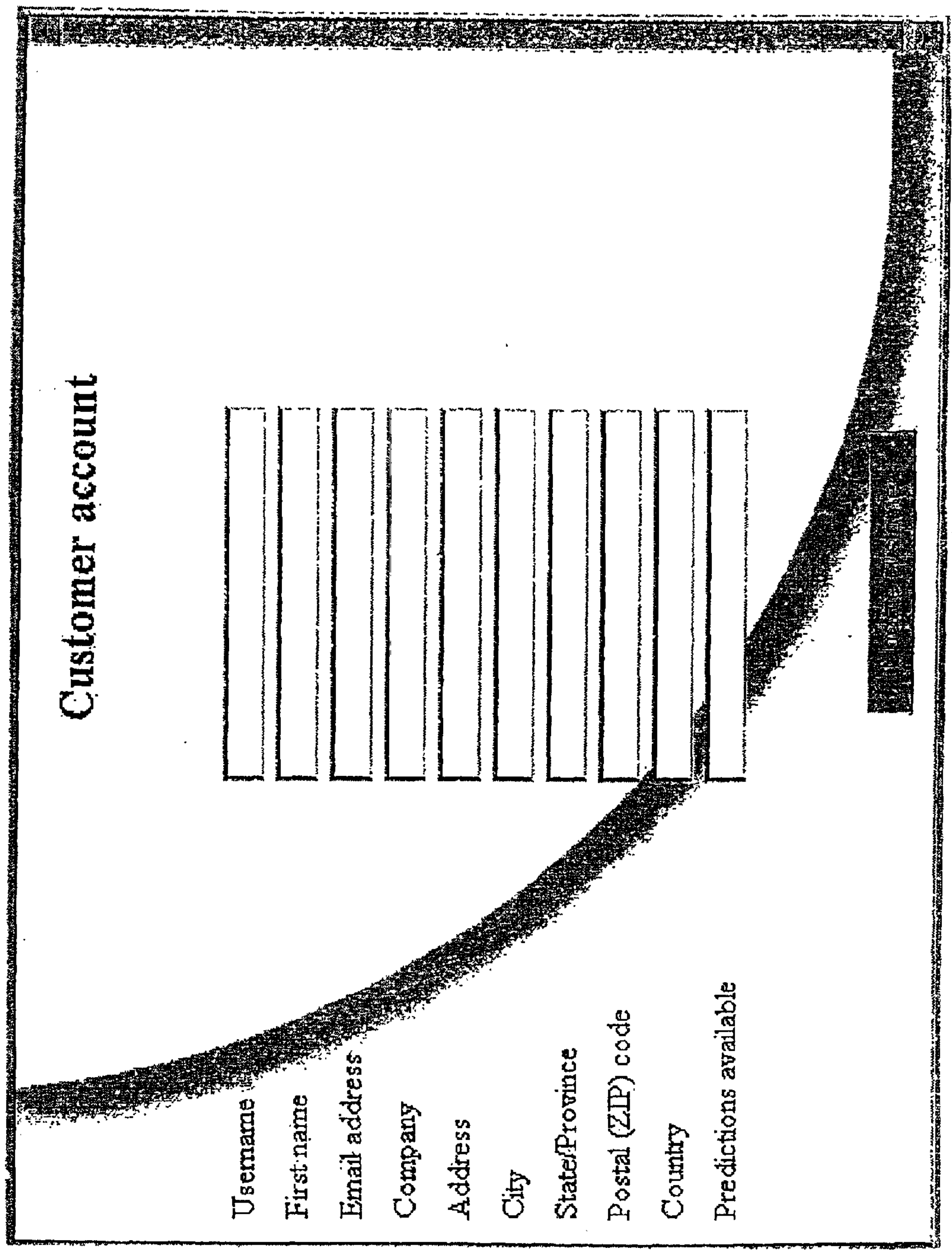
FIG. 7 illustrates an exemplary Web-based screen for collecting information from a customer to establish a customer account, according to the principles of the invention.

The opening of a customer account may also require the customer to provide information about the customer itself. FIG. 7 illustrates an exemplary Web-based screen for collecting information from a customer to establish a customer account. FIG. 7 illustrates the collection of, for example, the name of the customer and the customer's e-mail and mailing address. The account may also specify agreed-upon restrictions on the types of requests available to the customer. For example, the customer may be authorized to submit requests only for specific categories of materials and/or components whose content level is to be determined. The customer account may also contain information regarding any fee to be charged to the customer for predictions. As with any other collected information, any or all of the information may be stored, for example in information storage 170, and may be made accessible to the customer.

Another embodiment of the invention is a fee structure for payment by the customer for the prediction service and reports. The fee may be based, for example, on an agreement with the customer to submit a certain minimum number of requests within a certain period of time. The fee may be charged, for example, on a quarterly basis per year based on an expected number of requests within each quarter. An agreement may be reached with the customer to submit a certain number of requests every quarter for a duration of several years, for example three years. A fixed fee may be charged to the customer every quarter, for example at the beginning of each quarter, based on that expected number of requests. In the event that the total number of requests during a year exceed the expected number of samples for that year, an additional fee may be imposed at the end of the year as a charge for the excess requests.

Any fee structure, including those described above, may furthermore be modified as a function of the number of requests the customer expects to or actually does make. For example, a more favorable fee structure per prediction may apply to a customer who makes 5000 requests per year compared to a customer who makes 1000 requests per year. Other factors that may affect the fee structure include, for example, the number of component content levels to be predicted in each request, the prediction type (for example, total v. digestible, or methionine v. lysine), and any particular desired time of response requested by the customer. For example, determination of two content levels that require analysis using two different calibrations may be priced higher than determination of only one content level. Furthermore, any agreement involving service and pricing with the customer may be in the form of, for example, a renewable or non-renewable contract.

The fee structure may also make certain exceptions for predictions that carry an accompanying degree of error that exceeds a certain threshold value. For example, a prediction that carries an error above a threshold value could be termed an "outlier," and its accompanying prediction may be reported at no cost to the customer. Thus, any outliers would not count towards any minimum number of requests the customer has agreed to submit. Alternatively, an agreement could be reached with the customer to allow a maximum number of outliers made available free of charge. For example, an agreement could be reached with the customer to process a fixed number of requests, including a certain maximum number of outliers. Any outliers processed above that maximum would nonetheless be treated as normal predictions for pricing purposes.

In the event that an outlier is found during analysis of a spectrum, an offer may be made to the customer to determine a more accurate measurement of the content level of the component through conventional means and at no cost to the customer. If the customer accepts the offer, the customer may ship the material of interest to the offeror, and the offeror may perform a conventional measurement and report the more accurate result to the customer. The spectra of the material may then be correlated with the more accurate content level of component, and that information may be added to the database to enrich or create calibrations in the database. Such a process allows for the continuous refining of existing database calibrations and the evolution of new calibrations.

For purposes of tracking the number of customer requests made in a given time, and the number of any outliers reported, reporting unit 160 may provide that information to information storage 170. For example, reporting unit 160 may signal information storage 170 upon issuing any report. Information storage 170 could therefore store an up-to-date total of the number of customer requests made in a given time period. Reporting unit 160 may also signal information storage 170 when an outlier is reported, allowing that information to be stored as well. The running totals maintained in the information storage may be made retrievable by the customer.

Consistent with the principles of the invention, systems are provided that comprise:

means for electronically receiving a request from a customer to predict the content level of at least one component in a material, wherein the request includes a near infrared reflectance spectrum of the material;

means for comparing the spectrum to a database calibration that correlates known content levels of the component in other material to known near infrared reflectance spectra of the other material;

means for predicting the content level of the component; and means for electronically reporting the prediction to the customer.

Such systems and the means for performing the recited functions are described above.

Another embodiment of the invention is a method for obtaining a prediction of the content level of at least one component in a material, which comprises submitting a spectrum and request to the system and receiving the prediction from the system. This method is practiced, for example, by the customer who submits the request and receives the reported prediction.

Another embodiment of the invention is a method for evaluating the stability of a material over time. Stability of a material may be determined by, for example, observing any change in the content level of one or more components in the material. Such an analysis can be useful to evaluate the stability of materials during storage and in different storage environments. The method comprises obtaining a prediction for a material, obtaining a subsequent prediction of the material at a later time, and comparing the predictions to evaluate any change in the material.

The invention as claimed is not limited to the particulars of the embodiments disclosed in this specification. For example, the individual features of each of the disclosed embodiments may be combined or added to the features of other embodiments. In addition, the steps of the disclosed methods may be combined or modified without departing from the spirit of the invention as claimed. Accordingly, it is intended that the specification and examples be considered as exemplary only, with the true scope and spirit of the invention being indicated by the following claims.

What is claimed is:

1. A method comprising:

electronically receiving a request from a customer to predict the content level of at least one component in a feedstuff, wherein the request includes a near infrared reflectance spectrum of the feedstuff and the component is selected from proteins, total or digestible amino acids, gross or metabolizable energy, total or retained phosphorous, an impurity and a toxin;

comparing the spectrum to a specific database calibration that correlates known content levels of the component in other feedstuff to known near infrared reflectance spectra specific of the other feedstuff predicting the content level of the component; and electronically reporting the prediction to the customer;

said method further comprising determining that an outliner exists when the prediction of the content level of the component has a degree of error that exceeds a predetermined threshold value; and providing the prediction report to the customer at no cost when the prediction of the content level is determination to be an outlier.

2. A method as claimed in claim 1, wherein the calibration includes at least one correlation between a known content level of the component determined by in vivo measurement and a near infrared reflectance spectra of the feedstuff containing that component.

3. A method as claimed in claim 1, wherein the feedstuff is cereal, corn, soybean cake, oleoproteinaceous flour, animal meal, animal byproduct, fish meal, cereal byproduct, or silage corn.

4. A method as claimed in claim 1, wherein the at least one component is total or digestible methionine, lysine, cystine, threonine, tryptophane, valine, isoleucine, phenylalanine, histidine or arginine.

5. A method as claimed in claim 1, which comprises presenting one or more menu options for selection by the customer in making the customer request.

6. A method as claimed in claim 5, which comprises presenting to the customer menu options for the report format of the prediction report.

7. A method as claimed in claim 5, which comprises presenting to the customer menu options for the category of feedstuff represented by the spectrum.

8. A method as claimed in claim 5, which comprises presenting to the customer menu options for one or more components whose content level is to be predicted.

9. A method as claimed in claim 1, which comprises reporting the prediction to the customer within 24 hours of the customer request.

10. A method as claimed in claim 1, which comprises reporting the prediction to the customer within 10 minutes of the customer request.

11. A method as claimed in claim 1, wherein the customer request and the prediction report may be exchanged 24 hours a day.

12. A method as claimed in claim 1, which comprises providing the customer with one or more identity and/or security codes for use by the customer in making a request.

13. A method as claimed in claim 1, which comprises verifying the one or more identity and/or security codes upon receipt of a request.

14. A method as claimed in claim 1, which comprises storing the customer request and prediction report of one or more customer requests.

15. A method as claimed in claim 14, wherein the stored information may be retrieved by the customer upon request.

16. A method as claimed in claim 15, wherein the stored information may be retrieved by the customer on a Web site.

17. A method as claimed in claim 1, further comprising providing a central database with calibrations based on samples taken from geographically diverse regions, wherein the calibrations of the central database comprise the specific database calibration for predicting the content level of the component.

18. A method as claimed in claim 1, further comprising providing a central database with calibrations based on materials produced in different seasons of the year, wherein the calibrations of the central database comprise the specific database calibration for predicting the content level of the component.

19. A method as claimed in claim 1, further comprising:

presenting, when the prediction of the content level is determined to be an outliner, an offer to the customer to perform a measurement of the content level of the component based on a sample of the feedstuff; and in response to an acceptance of the offer by the customer, measuring the content level of the component in the sample of the feedstuff and reporting the results of the measurement to the customer.

20. A method as claimed in claim 1, further comprising correlating a near infrared reflectance spectrum of the sample of the feedstuff with the measured content level of component to produce calibration data and adding the calibration data to a central database to enrich the database for handling future customer requests.

* * * * *